United States Patent [19]
Li et al.

[11] Patent Number: 5,763,602
[45] Date of Patent: Jun. 9, 1998

[54] METHODS OF SYNTHESES OF PHTHALOCYANINE COMPOUNDS

[76] Inventors: Ying-Syi Li, 12700 Fairhill, Apt. 401, Shaker Hts., Ohio 44120; Malcolm E. Kenney, 1203 Hereford Rd., Cleveland Hts., Ohio 44118

[21] Appl. No.: 724,347

[22] Filed: Oct. 1, 1996

[51] Int. Cl.$^6$ .......................... C09B 47/04; C09B 47/08; C07F 7/18
[52] U.S. Cl. .............................. 540/128; 514/63
[58] Field of Search ................... 540/128; 514/63

[56] References Cited

U.S. PATENT DOCUMENTS

| | | | |
|---|---|---|---|
| 4,927,735 | 5/1990 | Era et al. | 430/270 |
| 5,166,197 | 11/1992 | Kenney et al. | 514/63 |
| 5,358,940 | 10/1994 | Capraro et al. | 540/4 |
| 5,484,778 | 1/1996 | Kenney et al. | 514/63 |

OTHER PUBLICATIONS

"Silicon Phthalocyanine/Methyl Methacrylate Copolymer Slab Directional Couplers for All-Optical Switching" by Sounik, et al., *Journal of Applied Polymer Science*, vol. 53, pp. 677–685, (1994).

"Synthesis of Ampjiphilic Phthalocyanines and Langmuir–Blodgett Film Balance Studies of These Compounds" by Batzel, submitted in partial fulfillment of requirements for degree of Doctor of Philosophy, Dept. of Chemistry, Case Western Reserve University, Mar. 26, 1990. (Entered in OCLC/Cataloged 21265660).

"The Synthesis, Photophysical and Photobiological Properties, and In Vitro Structure–Activity Relationships of a Set of Silicon Phthalocyanine PDT Photosensitizers" by He, et al., *Photochem. Photobiol.*, vol. 65, No. 3, Mar. 1997, pp. 581–586.

Abstract 126:239641s "Organosilicon (na)phthalocyanine photoactivators and cleaning compositions containing them" by A.D. Wiley, *CA Selects Plus: Organosilicon Chemistry*, Issue 9, 1997, p. 43.

Abstract 126:239642t "Low–hue photodisinfectants", by A.D. Wiley, *CA Selects Plus: Organosilicon Chemistry*, Issue 9, 1997, p. 43.

U.S. application Ser. No. 08/829,527, filed Mar. 28, 1997.

"New Phthalocyanine Photosensitizers for Photodynamic Therapy," by Oleinick et al., *Photochemistry and Photobiology*, vol. 57, No. 2, pp. 242–247, Feb. 1993.

"DNA Lesions and DNA Degradation in Mouse Lymphoma L5178Y Cells After Photodynamic Treatment Sensitized by Chloraluminum Phthalocyanine," by Ramakrishnan et al., *Photochemistry and Photobiology*, vol. 50, No. 3, pp. 373–378, Sep. 1989.

"Photodynamic Therapy Induces Rapid Cell Death by Apoptosis in L5178Y Mouse Lymphoma Cells," by Agarwal et al., *Cancer Research*, vol. 51, No. 51, pp. 5993–5996, Nov. 1, 1991.

"The Phthalocyanines: A New Class of Mammalian Cell Photosensitizers With a Potential for Cancer Phototherapy," by Ben–Hur et al., *Int. J. Radiat. Biol.*, vol. 47, No. 2, pp. 145–147, Feb. 1985.

"Activity of Phthalocyanine Photosensitizers Against Human Glioblastoma in Vitro," by Abernathy et al., *Neurosurgery*, 21, No. 4, pp. 468–473, Oct. 1987.

"The Role of Singlet Oxygen in the Photoemolysis of Red Blood Cells Sensitized by Phthalocyanine Sulfonates," by Sonoda et al., *Photochem. Photobiol.*, vol. 46, No. 5, pp. 625–631, Nov. 1987.

"Evaluation of Sulfonated Aluminum Phthalocyanines for Use in Photochemotherapy," by Berg et al., *Cancer Letters*, vol. 44, pp. 7–15, 1989.

"The Effect of Substitutents on Phthalocyanine Phototoxicity," by Rosenthal et al., *Photochem. Photobiol.*, vol. 46, No. 6, pp. 959–963, Dec. 1987.

"Synthesis and Photocytotoxicity of Some New Substituted Phthalocyanines," by Leznoff et al., *Photochem. Photobiol.*, vol. 49, pp. 279–284, Mar. 1989.

*The Merck Manual*, 15th Edition, Robert Berkow, ed., pp. 1219–1220, 1227.

"The Nuclear Magnetic Resonance Spectra and the Electronic Spectra of Some Silicon and Germanium Phthalocyanines," Kane et al., *Inorganic Chemistry*, vol. 9, pp. 1445–1448.

"Photodynamic Therapy With Phthalocyanine Photosensitisation: Quantitative Studies in a Transplantable Rat Fibrosarcoma," by Tralau et al., *Br. J. Cancer*, vol. 55, No. 4, pp. 389–395, Apr. 1987.

(List continued on next page.)

*Primary Examiner*—John M. Ford
*Assistant Examiner*—Pavanaram K. Sripada
*Attorney, Agent, or Firm*—Calfee, Halter & Griswold

[57] ABSTRACT

The present invention provides improved methods for synthesizing phthalocyanines, particularly HOSiPcOSi$(CH_3)_2$$(CH_2)_3$N$(CH_3)_2$, which do not involve photolysis, and which produces purity of at least about 95%, and in the preferred embodiment of the first method of synthesis provide a yield of greater than about 70% and typically greater than 80%. The first method involves a method for synthesizing a phthalocyanine compound comprising the following steps: providing a phthalocyanine precursor having a central silicon; adding a first aminosiloxy ligand to the central silicon of the phthalocyanine precursor; adding a second aminosiloxy ligand to the central silicon of the phthalocyanine precursor; displacing the second aminosiloxy ligand by an organic acid ligand, preferably Cl$_3$CCOO ligand; then displacing the Cl$_3$CCOO ligand with an HO ligand. The second method for making Pc4 is a method for synthesizing a phthalocyanine compound comprising the following steps: providing a phthalocyanine precursor having a central silicon; providing a siloxy ligand with an iodo group; adding a first and second siloxyiodo ligand to the central silicon of the phthalocyanine precursor; displacing the second siloxyiodo ligand by an organic acid, preferably a Cl$_3$CCOO ligand; then displacing the a Cl$_3$CCOO ligand with an HO ligand; and then displacing the iodo group with a dimethylamino group.

12 Claims, No Drawings

OTHER PUBLICATIONS

"Biological Activities of Phthalocyanines—IX. Photosensitization of V-79 Chinese Hamster Cells and EMT-6 Mouse MAmmary Tumor by Selectively Sulfonated Zinc Phthalocyanines," by Brasseur et al., *Photochem. Photobiol.*, vol. 47, No. 5, pp. 705-711, May 1988.

"Tissue Uptake, Distribution and Potency of the Photoactivable Dye Chloraluminum Sulfonated Phthalocyanine in Mice Bearing Transplantable Tumors," by Chan et al., *Cancer Res.*, vol. 48, No. 11, pp. 3040-3044, Jun. 1, 1988.

"Photodynamic Therapy for Experimental Intraocular Melanoma Using Chloroaluminum Sulfonated Phthalocyanine," *Arch. Ophthalmol.*, vol. 107, pp. 886-890, Jun. 1989.

"Synthesis of Positively Charged Phthalocyanines and Their Activity in the Photodynamic Therapy of Cancer Cells," by Wohrle et al., *Photochem. Photobiol.*, vol. 51, No. 3, pp. 351-356, Mar. 1990.

"Laser-Induced Photodynamic Therapy With Aluminum Phthalocyanine Tetrasulfonate as the Photosensitizer: Differential Phototoxicity in Normal and Malignant Human Cells in Vitro," by Glassberg et al., *J. Inv. Dermatol.*, vol. 94, No. 5, pp. 604-610, May 1990.

"Photodynamic Therapy of Spontaneous Cancers in Felines, Canines, and Snakes With Chloro-Aluminum Sulfonated Phthalocyanine," by Roberts et al., *J. Natl. Cancer Inst.*, vol. 83, No. 1, p. 1823, Jan. 2, 1991.

"Inactivation of Viruses in Red Cell and Platelet Concentrates With Aluminum Phthalocyanine (AlPc) Sulfonates," by Horowitz et al., *Blood Cells*, vol. 18, No. 1, pp. 141-150, Jan. 1992.

"Photodynamic Therapy of Chemically-and Ultraviolet B Radiation-Induced Murine Skin Papillomas by Chloroaluminum Phthalocyanine Tetrasulfonate," by Agarwal et al., *Photochem. Photobiol.*, vol. 56, No. 1, pp. 43-50, Jul. 1992.

"Biological Activities of Phthalocyanines—XVI. Tetrahydroxy-and Tetraalkylhydroxy Zinc Phthalocyanines. Effect of Alkyl Chain Length on In Vitro and In Vivo Photodynamic Activities," by Boyle et al., *Br. J. Cancer*, vol. 67, No. 6, pp. 1177-1181, Jun. 1993.

"Phthalocyanines in Photobiology," by I. Rosenthal and E. Ben-Hur, in *Phthalocyanines: Properties and Applications*, ed. by C.C. Leznoff and A.B.P. Lever, VCH Publishers, Inc., New York, pp. 397-425, 1989.

"Preclinical Examination of First and Second Generation Photosensitizers Used in Photodynamic Therapy," by C.J. Gomer, *Photochem. Photobiol.*, vol. 54, No. 6, pp. 1093-1107, Dec. 1991.

"Photodynamic Therapy in Oncology: Mechanisms and Clinical Use," H.I. Pass, *J. Natl. Can. Inst.*, vol. 85, No. 6, pp. 443-456, Mar. 17, 1993.

"Phthalocyanines as Photodynamic Sensitizers," by I. Rosenthal, *Photochem. Photobiol.*, vol. 53, No. 6, pp. 859-870, Jun. 1991.

"Photodynamic effects of silicon phthalocyanines in model cells and tumors," by Oleinick, et al., SPIE vol. 1645, *Optical Methods for Tumor Treatment and Detection*, 1992, pp. 242-250.

Abstract 108:178915p "$\pi$-$\pi$ Interaction, architecture, and bandwidths in molecular metals," by Doris, et al., *Is. J. Chem.*, 1986.

Abstract 102:78944e "The $\pi$-$\pi$ Interactions and bandwidths in molecular metals", Ciliberto, et al., *J. Am. Chem. Soc.* 1984.

METHODS OF SYNTHESES OF PHTHALOCYANINE COMPOUNDS

BACKGROUND OF THE INVENTION

Conventional methods for synthesizing phthalocyanine pharmaceutical compounds, particularly HOSiPcOSi(CH$_3$)$_2$(CH$_2$)$_3$N(CH$_3$)$_2$, employ a blocking methyl group to prevent the addition of more than one aminosiloxy group on the central silicon of the phthalocyanine precursor. Once the aminosiloxy ligand has been added, this blocking group is displaced with the desired HO group through a photolysis step.

However, this method of synthesis has various disadvantages; photolysis requires unusual apparatus, is quite time consuming, and results in a relatively low yield, typically about 50 to 60% of the product. It would be desirable to have a method for synthesizing phthalocyanines, particularly HOSiPcOSi(CH$_3$)2(CH$_2$)$_3$N(CH$_3$)$_2$ that does not involve a photolysis step, and provides an improved yield.

SUMMARY OF THE INVENTION

The present invention provides improved methods for synthesizing phthalocyanines, particularly HOSiPcOSi(CH$_3$)2(CH$_2$)$_3$N(CH$_3$)$_2$, which do not involve photolysis, and which produce a purity of at least about 95%, and in the preferred embodiment of the first method of synthesizing Pc 4, provide a yield of greater than about 70% and typically greater than 80%. The first method involves a method for synthesizing a phthalocyanine compound comprising the following steps: providing a phthalocyanine precursor having a central silicon; adding a first aminosiloxy ligand to the central silicon of the phthalocyanine precursor; adding a second aminosiloxy ligand to the central silicon of the phthalocyanine precursor; displacing the second aminosiloxy ligand by an organic acid ligand, preferably a Cl$_3$CCOO ligand; then displacing the Cl$_3$CCOO ligand with an HO ligand.

The second method for making Pc4 is a method for synthesizing a phthalocyanine compound comprising the following steps: providing a phthalocyanine precursor having a central silicon; providing a siloxy ligand with an iodo group; adding a first and second siloxyiodo ligand to the central silicon of the phthalocyanine precursor; displacing the second siloxyiodo ligand by an organic acid ligand, preferably a Cl$_3$CCOO ligand; then displacing the Cl$_3$CCOO ligand with an Ho ligand; and then displacing the iodo group with a dimethylamino group.

The invention also relates to methods for making two novel phthalocyanine compounds HOSiPcOSi (CH$_3$)$_2$(CH$_2$)$_3$I and SiPc[OSi(CH$_3$)$_2$(CH$_2$)$_3$I]$_2$, and to the compounds themselves which are useful as dyes and in photodynamic therapy.

DESCRIPTION OF THE INVENTION

The methods of the present invention are useful in making phthalocyanine compounds having the following general structure:

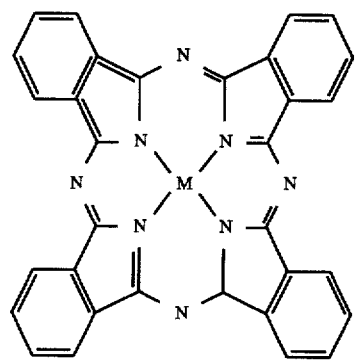

wherein:

M is (G)$_a$Y[(OSi(CH$_3$)$_2$(CH$_2$)$_b$N$_c$(R')$_d$(R")$_e$)$_f$X$_g$]$_p$

Y is Si;

R' is selected from the group of H, C, CH$_2$, CH$_3$, C$_2$H$_5$, C$_4$H$_9$, C$_4$H$_8$NH, C$_4$H$_8$N, C$_4$H$_8$NCH$_3$, C$_4$H$_8$S, C$_4$H$_8$O, C$_4$H$_8$Se, CH$_2$CH$_3$, (CH$_2$)$_3$(CH$_3$)$_2$, OC(O)CH$_3$, OC(O), (CH$_3$)$_2$(CH$_2$)$_{11}$, CS, CO, CSe, OH, C$_4$H$_8$N(CH$_2$)$_3$CH$_3$, (CH$_2$)$_3$N(CH$_3$)$_2$, C(O)C$_{27}$H$_{30}$N$_2$O, (CH$_2$)$_n$N((CH)$_O$(CH$_3$))$_2$, an alkyl group having from 1 to 12 carbon atoms;

R" is selected from the group of H, SO$_2$CH$_3$, (CH$_2$)$_2$N(CH$_3$)$_2$, (CH$_2$)$_{11}$CH$_3$, C(S)NHC$_6$H$_{11}$O$_5$, (CH$_2$)$_n$N((CH)$_O$(CH$_3$))$_2$, and an alkyl group having from 1 to 12 carbon atoms;

G is OH;

X is selected from the group of: I; F; Cl; or Br;

a=0 or 1;
b=an integer from 2 to 12;
c=0, 1;
d=0, 1, 2, or 3;
e=0, 1, or 2;
f=1;
g=0 or 1;
n=an integer from 1 to 12;
o=an integer from 1 to 11;
p=1 where a is 1,or 2 where a is 0.

Preferably, M is HOSiOSi (CH$_3$)$_2$(CH$_2$)$_3$N(CH$_3$)$_2$, HOSiOSi (CH$_3$)$_2$(CH$_2$)$_3$I or Si[OSi(CH$_3$)$_2$(CH$_2$)$_3$I]$_2$.

In the method for making Pc 4 of the prior art, the steps that are believed to occur are:

(1) 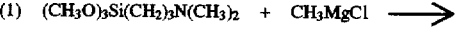 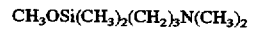

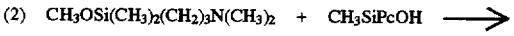

(2) 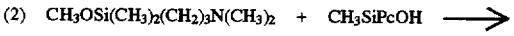 

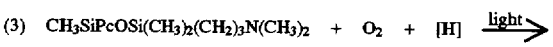

(3) 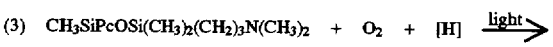 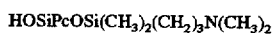

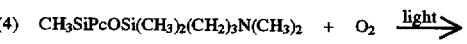

or (4) 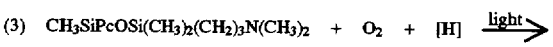 

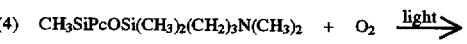

where "H" represents a source of hydrogen. The byproducts in reactions (3) and (4) are different. The prior art synthesis uses a blocking methyl group to prevent the addition of more than one aminosiloxy group on the central silicon of the phthalocyanine precursor. Then, after the aminosiloxy ligand has been added, this blocking group is displaced with the desired HO group through a photolysis step.

The First Method of Synthesizing Pc 4

In contrast to the prior art, the first new method of synthesis, avoids a photolysis step; an extra aminosiloxy ligand is added on the central silicon of the phthalocyanine precursor and then the sequential displacement of this extra ligand by an organic acid ligand, preferably a Cl$_3$CCOO ligand and the desired HO ligand. The organic acid is a non-mineral acid, which has an acidity of Cl$_3$CCOOH, is soluble in the organic solvent used in the reaction, and includes but is not limited to Cl$_3$CCOOH and Cl$_2$CHCOOH.

The first method involves a method for synthesizing a phthalocyanine compound comprising the following steps: providing a phthalocyanine precursor having a central silicon; adding a first aminosiloxy ligand to the central silicon of the phthalocyanine precursor; adding a second aminosiloxy ligand to the central silicon of the phthalocyanine precursor; displacing the second aminosiloxy ligand by an organic acid ligand, preferably a Cl$_3$CCOO ligand; then displacing the Cl$_3$CCOO ligand with an HO ligand.

The steps in the preferred embodiment of the first synthesis, that are believed to occur are summarized as:

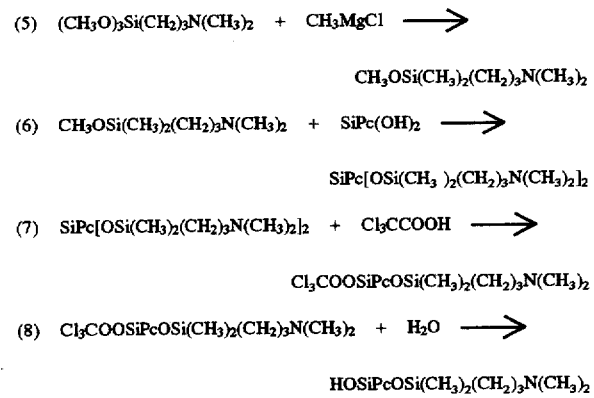

That is, the photolysis step is avoided; this results in a phthalocyanine product having an improved purity. The phthalocyanine produced according to the first improved method has a purity of about 98%; in contrast to the method of the prior art where the purity is about 95%. Further, the improved method provides a higher yield, that is, about 70% to 80%, rather than about 50% to 60%.

The Second Synthesis of Pc 4

The second synthesis of HOSiPcOSi(CH$_3$)$_2$(CH$_2$)$_3$N(CH$_3$)$_2$ uses a different approach from both the prior art and the first method. The second method for making Pc 4 is a method for synthesizing a phthalocyanine compound comprising the following steps: providing a phthalocyanine precursor having a central silicon; providing a siloxy ligand with an iodo group; adding a first and second siloxyiodo ligand to the central silicon of the phthalocyanine precursor; displacing the second siloxyiodo ligand by an organic acid ligand, preferably a Cl$_3$CCOO ligand; then displacing the Cl$_3$CCOO ligand with an HO ligand; and then displacing the iodo group with a dimethylamino group.

The steps that probably occur in the preferred embodiment of the second method of synthesis of Pc 4 can be summarized as:

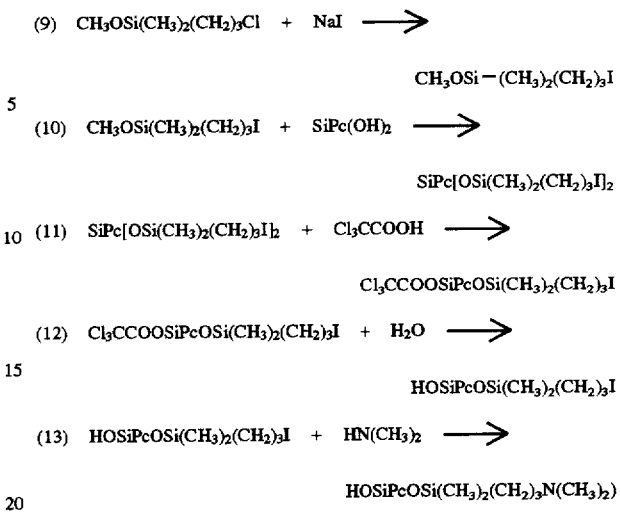

In the second method for making Pc 4, a hydroxysiloxy-silicon phthalocyanine in which the siloxy ligand terminates in an iodo group is first formed. Then, in the final reaction the iodo group is displaced with the desired dimethylamino group. Thus, in this approach the aminosiloxy ligand is built up stepwise on the phthalocyanine rather than being formed separately. The Pc4 produced according to the second improved method have a purity of about 98%; in contrast to the methods of the prior art where the purity is about 95%.

This second synthesis is particularly useful because it offers a procedure for making Pc 4 labeled with $_{14}$C. The reagent $^{14}$C labeled NH(CH$_3$)$_2$ is added in the last step of the method, preferably with unlabeled with HN(CH$_3$)$_2$. Suitable $^{14}$C labeled NH(CH$_3$)$_2$ is commercially available from New England Nuclear Corporation, 549 Albany Street, Boston, Mass. 02118 and Amersham Life Science, Inc., 2636 South Clearbrook Drive, Arlington Heights, Ill. The $^{14}$C labeled Pc 4 is useful reagent for pharmacokinetic studies of Pc 4.

Compounds HOSiPcOSi(CH$_3$)$_2$(CH$_2$)$_3$I and SiPc[OSi(CH$_3$)$_2$(CH$_2$)$_3$I]$_2$, which are made as intermediates in the method for making Pc 4, are also useful in photodynamic therapy, including therapies disclosed in U.S. Pat. No. 5,166,197, issued Nov. 24, 1992, to Kenney et. al.; U.S. Pat. No. 5,484,778, issued Jan. 16, 1996, to Kenney et. al.; and in "New Phthalocyanine Photosensitizers for Photodynamic Therapy", Oleinick, et. al. *Photochemistry and Photobiology*, (1993), Volume 57, pages 242–247, which are specifically incorporated herein by refeence. Compounds HOSiPcOSi(CH$_3$)$_2$(CH$_2$)$_3$I and SiPc[OSi(CH$_3$)$_2$(CH$_2$)$_3$I]$_2$, are also useful as reagents, and for experimental and research.

The following examples are intended to be illustrative only and not intended to in any way limit the scope of the invention.

EXAMPLE 1

Preferred Method for Synthesis of HOSiPcOSi(CH$_3$)$_2$(CH$_2$)$_3$N(CH$_3$)$_2$, Pc 4

HOSiPcOSi(CH$_3$)$_2$(CH$_2$)$_3$N(CH$_3$)$_2$, Pc 4, was made by a synthesis in which CH$_3$OSi(CH$_3$)$_2$(CH$_2$)$_3$N(CH$_3$)$_2$, SiPc[OSi(CH$_3$)$_2$(CH$_2$)$_3$N(CH$_3$)$_2$]$_2$ (Pc 12), Cl$_3$CCOOSiPcOSi(CH$_3$)$_2$(CH$_2$)$_3$N(CH$_3$)$_2$, and finally Pc 4 were prepared in sequence.

Preparation of CH$_3$OSi(CH$_3$)$_2$(CH$_2$)$_3$N(CH$_3$)$_2$ CH$_3$OSi(CH$_3$)$_2$(CH$_2$)$_3$N(CH$_3$)$_2$ was prepared as described in U.S. Pat. No. 5,166,197, issued Nov. 24, 1992, to Kenney et al. and in "New Phthalocyanine Photosensitizers for Photodynamic Therapy", Oleinick, et. al. *Photochemistry and Photobiology.* 1993, volume 57, pages 242–247, at page 243.

Preparation of SiPc[OSi($CH_3$)$_2$($CH_2$)$_3$N($CH_3$)$_2$]$_2$ Pc 12.

A mixture of 980 mg, 5.59 mmol of $CH_3$OSi($CH_3$)$_2$($CH_2$)$_3$N($CH_3$)$_2$ and a suspension of 400 mg, 0.697 mmol SiPc(OH)$_2$ and 400 mL pyridine that had been dried by distillation (about 20 mL of distillate), was slowly distilled for 3 hours (about 20 mL of distillate) and then filtered. The filtrate was evaporated to dryness with a rotary evaporator at about 40° C., and the solid was washed with an 2:3, 150 mL ethanol-water solution, then dried at about 60 torr, about 70° C. and weighed 552 mg. NMR analysis revealed :(300 MHz, $CDCl_3$): delta 9.61 (m, 1,4-Pc H), 8.31 (m, 2,3-Pc H), 1.60 (s, $NCH_3$), 0.82 (m, gamma-$CH_2$), −1.12 (m, beta-$CH_2$), −2.30 (m, alpha-$CH_2$), −2.91 (s, $SiCH_3$). The resulting SiPc[OSi($CH_3$)$_2$($CH_2$)$_3$N($CH_3$)$_2$]$_2$ which is blue, is soluble in dimethylformamide and $CH_2Cl_2$, and is insoluble in hexanes and water.

Preparation of $Cl_3$CCOOSiPcOSi($CH_3$)$_2$($CH_2$)$_3$N($CH_3$)$_2$

A solution of 552 mg of SiPc[OSi($CH_3$)$_2$($CH_2$)$_3$N($CH_3$)$_2$]$_2$ also referred to herein as "Pc 12", 590 mg, 3.61 mmol trichloroacetic acid, and 90 mL $CH_2Cl_2$, was stirred at room temperature for 5 hours. The resultant was mixed with 90 mL pyridine and then with 90 mL $H_2O$, and the mixture formed was separated. The aqueous layer was washed with 100 mL $CH_2Cl_2$, the washings were filtered, and the residue was washed with 200 mL $CH_2Cl_2$ The organic layer was filtered, and the filtrate and $CH_2Cl_2$ washings were combined and evaporated to dryness with a rotary evaporator at about 40° C. The solid was dried at about 60 torr, and at about 60° C. to provide 647 mg of the blue-green compound, $Cl_3$CCOOSiPcOSi-($CH_3$)$_2$($CH_2$)$_3$N($CH_3$)$_2$. NMR analysis revealed; (300 MHz, $CDCl_3$) delta 9.68 (m, 1,4-Pc H), 8.19 (m, 2,3-Pc H), 1.61 (s, $NCH_3$), 0.85 (m, gamma-$CH_2$), −1.03 (m, beta-$CH_2$), −2.16 (m, alpha-$CH_2$), −2.78 (s, $SiCH_3$).

Preparation of HOSiPcOSi($CH_3$)$_2$($CH_2$)$_3$N($CH_3$)$_2$, Pc 4

A solution of 647 mg $Cl_3$CCOOSiPcOSi($CH_3$)$_2$($CH_2$)$_3$N($CH_3$)$_2$ and 20 mL $CH_2Cl_2$ was passed down a 3×24 cm chromatography column composed of $Al_2O_3$ V. The loaded column was then eluted with a solution of 1.5 parts $CH_2Cl_2$-ethyl acetate, and the eluate was evaporated to dryness with a rotary evaporator at about 40° C. The solid was extracted into 20 mL $CH_2Cl_2$, recovered by evaporating the extract with a rotary evaporator, dissolved in 3 ml of $CH_2Cl_2$, and precipitated with 12 mL pentane. The precipitate was recovered by filtration, washed with a 1:4, 15 mL of $CH_2Cl_2$-pentane solution and 20 mL pentanedried at about 60 torr, 60° C. and weighed (416 mg, 0.580 mmol, 83% based on SiPc(OH)$_2$ used). UV-vis (dimethylformamide) lambda$_{max}$ (nm); epsilon ($M^{-1}cm^{-1}$): 668; 230,000. NMR analysis revealed (300 MHz, 8.4 mM, $CDCl_3$): delta 9.11 (m, 1,4-Pc H), 8.18 (m, 2,3-Pc H), 1.35 (s, $NCH_3$), 0.60 (m, gamma-$CH_2$), −1.36 (m, beta-$CH_2$), −2.49 (m, alpha-$CH_2$), −2.66 (s, SiOH), −3.10 (s, $SiCH_3$).

EXAMPLE 2

Second Method for Synthesis of Pc 4.

Pc 4 was also made by a synthesis in which $CH_3$OSi($CH_3$)$_2$($CH_2$)$_3$I, SiPc[OSi($CH_3$)$_2$($CH_2$)$_3$I]$_2$ also referred to herein as "Pc 59", HOSiPcOSi($CH_3$)$_2$($CH_2$)$_3$I also referred to herein as "Pc 58", and finally Pc 4 were prepared in sequence.

Preparation of $CH_3$OSi($CH_3$)$_2$($CH_2$)$_3$I

A mixture of 10.6 g, 0.0700 mol $CH_3$OSi($CH_3$)$_2$($CH_2$)$_3$Cl, 20.8 g, 0.105 mol NaI and 100 mL acetone was refluxed for 2 days and filtered. The solid was washed with 50 mL acetone, and the washings and filtrate were combined and concentrated with a rotary evaporator at about 30° C. The concentrate was mixed with 50 mL ether, and the resulting suspension was filtered. The solid was washed with 100 ml ether, and the washings and the filtrate were combined and concentrated with a rotary evaporator at about 30° C. The concentrate weighed 14.9 g. NMR analysis at 200 MHz, in $CDCl_3$ revealed: delta 3.40 (s, $CH_3$O ), 3.17 (m, gamma-$CH_2$), 1.84 (m, beta-$CH_2$), 0.67 (m, alpha-$CH_2$), 0.08 (s, $SiCH_3$). The $CH_3$OSi($CH_3$)$_2$($CH_2$)$_3$I is a yellow, mobile liquid.

Preparation of SiPc[OSi($CH_3$)$_2$($CH_2$)$_3$I]$_2$

A mixture of 1.80 g $CH_3$OSi($CH_3$)$_2$($CH_2$)$_3$I, 401 mg, 0.698 mmol SiPc(OH)$_2$ and 300 mL xylene was slowly distilled for 6 hours to produce about 35 mL of distillate, and the mixture was evaporated to dryness with a rotary evaporator at about 50° C. The solid was washed with 75 mL ethanol and a 1:1, 70 mL ethanol-water solution, then dried at about 60 torr, 60° C., and weighed (567 mg, 0.537 mmol, 77 %). NMR analysis at 300 MHz, in $CDCl_3$ revealed: delta 9.65 (m, 1,4-Pc H), 8.34 (m, 2,3-Pc H), 1.75 (m, gamma-$CH_2$), −0.84 (m, beta-$CH_2$), −2.21 (m, alpha-$CH_2$), −2.87 (s, $SiCH_3$). The SiPc[OSi($CH_3$)$_2$($CH_2$)$_3$I]$_2$,which is blue, is soluble in dimethylformamide and $CH_2Cl_2$ and is insoluble in hexanes and water.

Preparation of HOSiPcOSi($CH_3$)$_2$($CH_2$)$_3$I

A solution of 514 mg, 0.488 mmol unchromatographed SiPc[OSi($CH_3$)$_2$($CH_2$)$_3$I]$_2$, 1.64 g, 10.0 mmol, trichioroacetic acid and 250 mL $CH_2Cl_2$ was stirred at room temperature for 5 hours, then mixed with 100 ML pyridine and then with 100 mL $H_2O$. The aqueous layer was washed with 60 mL $CH_2Cl_2$, the washings were filtered, and the residue was washed with 100 mL $CH_2Cl_2$. The organic layer was filtered and the filtrate and $CH_2Cl_2$ washings were combined and evaporated to dryness with a rotary evaporator (about 40° C.). The solid was chromatographed on an $Al_2O_3$ V substrate, with $CH_2Cl_2$-ethyl acetate, in a 1:1 ratio, dissolved in 4 mL $CH_2Cl_2$, precipitated with 6 mL pentane, recovered by filtration, washed with 20 mL pentane and a 1:1, 20 mL ethanol-water solution, dried at about 60 torr, about 60° C. and weighed (188 mg, 0.235 mmol, 48%). NMR analysis revealed (300 MHz, 7.0 mM, $CDCl_3$): delta 9.22 (m, 1,4-Pc H), 8.22 (m, 2,3-Pc H), 1.59 (m, gamma-$CH_2$), −1.01 (m, beta-$CH_2$), −2.36 (m, alpha-$CH_2$), −3.04 (s, $SiCH_3$), −3.22 (s, SiOH). The HOSiPcOSi($CH_3$)$_2$($CH_2$)$_3$I, which is blue, is soluble in dimethylformamide and $CH_2Cl_2$ and is insoluble in hexanes and water.

Preparation of HOSiPcOSi($CH_3$)$_2$($CH_2$)$_3$N($CH_3$)$_2$, Pc 4, the Final Stage A stirred suspension of 30.9 mg, 0.0386 mmol HOSiPcOSi($CH_3$)$_2$($CH_2$)$_3$I, 5.2 mg, 0.038 mmol $K_2CO_3$, a solution of HN($CH_3$)$_2$ in 2M, 0.5 mL, 1 mmol tetrahydrofuran solution and 9.5 mL tetrahydrofuran in a pressure tube (15 mL) was warmed at about 60° C. for 48 hours and evaporated to dryness with a rotary evaporator at about 30° C. The solid was extracted into 20 mL $CH_2Cl_2$, recovered by evaporating the extract with a rotary evaporator (room temperature), dissolved in 1 mL $CH_2Cl_2$, precipitated with 4 mL pentane, recovered by filtration, washed with a solution of $CH_2Cl_2$ and 1:4, 15 mL pentane, 10 mL pentane and an 1:4, 10 mL ethanol-water solution, dried at about 60 torr, at about 60° C. and weighed (22.1 mg, 0.0308 mmol, 80%, 30% based on SiPc(OH)$_2$ used).

EXAMPLE 2a

The procedure of Example 2 was followed, except in the final stage a smaller ratio of HN($CH_3$)$_2$ to HOSiPcOSi($CH_3$)$_2$($CH_2$)$_3$I was employed. Specifically, a stirred suspension of 40.5 mg, 0.0506 mmol HOSiPcOSi($CH_3$)$_2$($CH_2$)$_3$I, Pc 58, 2.4 mg, 0.017 mmol $K_2CO_3$, a solution of $HN(CH_3)_2$ in 2M, 0.2 mL, 0.4 mmol tetrahydrofuran and 4.8 mL tetrahydrofuran (4.8 mL) in a 5 mL heavy-wall reaction vial was warmed at about 60° C. for 24 hours, and evaporated to dryness with a rotary evaporator at about 30° C. The solid was extracted into 20 mL $CH_2Cl_2$, recovered by evaporating the extract to dryness with a rotary evaporator at room temperature, dissolved in 1 mL $CH_2Cl_2$, precipitated with 4 mL pentane, recovered by filtration, washed with a 1:4, 15 mL $CH_2Cl_2$-pentane solution, 10 mL pentane and an 1:4, 10 mL ethanol-water solution, dried at about 60 torr, at about 60° C., chromatographed on a $Al_2O_3$ III substrate using ethyl acetate-methanol, in a ratio of 10:1, washed with 15 mL pentane and an 1:4, 10 mL ethanol-water solution, dried at about 60 torr, 60° C. and weighed (17.5 mg, 0.0243 mmol, 48%, 18% based on $SiPc(OH)_2$ used).

EXAMPLE 2b

The synthesis of Example 2 is followed, except that a metallic derivative of $HN(CH_3)_2$, preferably a group I metal derivative, including, for example $LiN(CH_3)_2$ and $NaN(CH_3)_2$, is substituted for $HN(CH_3)_2$. Since the halosiloxy phthalocyanine and the amine may be used in an approximately 1:1 ratio, and thus is more efficient.

EXAMPLE 2c

The procedure of Example 2 is followed except that a mixture of $^{14}C$ labeled $NH(CH_3)_2$ and $HN(CH_3)_2$, is added in the last reaction with, to provide Pc 4 labeled with $^{14}C$.

Although one embodiment of this invention has been shown and described, various adaptations and modifications can be made without departing from the scope of the invention as defined in the appended claims.

What is claimed is:

1. A method for synthesizing a phthalocyanine compound comprising the following steps:
   a. providing a phthalocyanine precursor having a central silicon;
   b. adding two aminosiloxy ligands to the central silicon of the phthalocyanine precursor;
   c. displacing one of the aminosiloxy ligands by an organic acid ligand;
   d. then displacing the organic acid ligand with an hydroxyl ligand;

to provide a phthalocyanine compound wherein the central silicon has an aminosiloxy lignads and an hydroxyl ligand.

2. The method of claim 1, wherein the phthalocyanine compound is $HOSiPcOSi(CH_3)_2(CH_2)_3N(CH_3)_2$, the phthalocyanine precursor is $SiPc(OH)_2$, and the amino siloxy ligand is $CH_3OSi(CH_3)_2(CH_2)_3N(CH_3)_2$.

3. The method of claim 2, wherein the organic acid ligand is $Cl_3CCOO$.

4. The method of claim 1, wherein the synthesis is further accomplished without photolysis.

5. A method for synthesizing a phthalocyanine compound comprising the following steps:
   a. providing a phthalocyanine precursor having a central silicon;
   b. providing a siloxy ligand with iodo group;
   c. adding a first and second siloxyiodo ligand to the central silicon of the phthalocyanine precursor.

6. The method of claim 4, wherein the phthalocyanine produced from step c is $SiPc[OSi(CH_3)_2(CH_2)_3I]_2$.

7. The method of claim 5, further comprising the steps of:
   d. displacing one of the two siloxyiodo ligand by an organic acid ligand;
   e. then displacing the organic acid ligand with an HO ligand.

8. The method of claim 7, wherein the phthalocyanine produced from step e is $HOSiPcOSi(CH_3)_2(CH_2)_3I$.

9. The method of claim 5, further comprising the steps of:
   d. displacing one of the two siloxyiodo ligands by an organic acid ligand;
   e. then displacing the organic acid ligand with an HO ligand;
   f. then displacing the iodo group with a dimethylamino group.

10. The method of claim 9, wherein the phthalocyanine compound is $HOSiPcOSi(CH_3)_2(CH_2)_3N(CH_3)_2$ and the organic acid ligand is $Cl_3CCOO$ ligand.

11. The method of claim 9, wherein the dimethylamino group is $^{14}C$ labeled.

12. The method of claim 9, wherein the dimethylamine group is provided by a group I metal dimethylamine.

* * * * *